(12) United States Patent
Stantchev

(10) Patent No.: US 7,959,355 B2
(45) Date of Patent: Jun. 14, 2011

(54) METHOD AND APPARATUS FOR IMAGING USING DIGITAL DENTAL X-RAY SENSOR

(76) Inventor: George Stantchev, Phoenix, AZ (US)

( * ) Notice: Subject to any disclaimer, the term of this patent is extended or adjusted under 35 U.S.C. 154(b) by 180 days.

(21) Appl. No.: 11/561,412

(22) Filed: Nov. 19, 2006

(65) Prior Publication Data

US 2008/0118028 A1   May 22, 2008

(51) Int. Cl.
*A61B 6/14* (2006.01)
(52) U.S. Cl. .......................... 378/191; 378/167; 378/168
(58) Field of Classification Search .......... 378/167–169, 378/175, 176, 191
See application file for complete search history.

(56) References Cited

U.S. PATENT DOCUMENTS

| | | | |
|---|---|---|---|
| 4,654,795 A * | 3/1987 | Shimoni | 250/363.07 |
| 6,527,442 B2 * | 3/2003 | Carroll | 378/189 |
| 6,762,791 B1 * | 7/2004 | Schuetzle | 348/231.3 |
| 2002/0060554 A1 * | 5/2002 | Odaohhara et al. | 320/134 |
| 2002/0141217 A1 * | 10/2002 | Cohen et al. | 363/146 |
| 2002/0171566 A1 * | 11/2002 | Huang et al. | 341/50 |
| 2003/0085621 A1 * | 5/2003 | Potega | 307/18 |
| 2005/0104900 A1 * | 5/2005 | Toyama et al. | 345/629 |
| 2005/0134708 A1 * | 6/2005 | Lee et al. | 348/240.2 |
| 2005/0220272 A1 * | 10/2005 | Glazer | 378/168 |
| 2006/0067463 A1 * | 3/2006 | Hack et al. | 378/38 |

* cited by examiner

*Primary Examiner* — Hoon Song
*Assistant Examiner* — Mona M Sanei

(57) ABSTRACT

A method and apparatus including an intraoral dental X-ray electronic sensor facing an x-ray source and connected to a signal processing unit that allows taking and storing multiple x-ray images even without the unit to be connected to database computer. The processing unit has a memory that may be equipped with energy source and the unit is mounted on the sensor holder and can be easily removed from it. The images from the memory can be downloaded into a database using standard serial digital interfaces during or after the image acquisition.

19 Claims, 4 Drawing Sheets

METHOD AND APPARATUS FOR IMAGING USING DIGITAL DENTAL X-RAY SENSOR

Providing advanced dental services require continuous improvement in the quality and convenience of the dental procedures. This invention offers a method and apparatus for dental imaging that provides ultimate simplicity, easy operation and patient comfort in taking full mouth dental x-ray series (FMS), further referred only as image series. The process of taking FMS includes composing up to 18 images four bitewings, eight posterior periapicals and six anterior periapicals.

SUMMARY OF THE INVENTION

The current invention is an apparatus comprising an intraoral dental X-ray sensor facing an x-ray source. The sensor is connected to a signal processing unit that allows taking and storing multiple x-ray images without the sensor to be connected to a storage database.

The digital dental radiography sensor system consists of and is not limited to CCD or CMOS pixel array encapsulated in protective enclosure, wired to a signal processing unit that converts the analog signal to digital and further to manage the digital information into storage device and/or to interface other devices.

Beside managing and storing images the signal processing unit also provides driving signals to the sensor. The sensor and the signal processing unit are powered from power source as example power delivered over the chosen interface or battery source.

The image is stored to internal memory either in encrypted or a standard image format and can be accessed from the computer using the serial interface. The internal memory of the signal processing unit can be mapped as additional memory to the computer when the device is connected.

The processing unit may be equipped with battery to provide sufficient power for taking a full mouth series. The device can be mounted on the sensor holder and can be easily removed from there. The images taken are stored in the memory and can be downloaded into a database using serial data interface.

Secondly the invention provides a method for image acquisition that allows taking multiple images without the need the sensor to be connected to image database. Taking the images is simple process as follow: (1) attaching the sensor and the processing unit to the holder, (2) activating the signal processing unit, (3) positioning the sensor holder, (4) positioning the x-ray head to face the sensor, (5) activating the x-ray unit, (6) repositioning the sensor and repeating steps 3 to 6 as long as it takes to complete the image series, (8) loading the images in the database.

The sensor is activated once and deactivated when the series is taken. The acquired images are stored in own memory as conventional formatted images or transferred using the serial interface if available during or after the image acquisition.

The images are digitally formatted and saved in the internal device memory using conventional image file format such as BMP, JPG, GIF, TIF, etc. and can be retrieved and displayed without additional processing or need of proprietary interface.

The processing unit may be equipped with proper indication for the image acquisition process and/or indication for the quality of the image. After the dental image series is completed the battery unit is unplugged and placed for charging on a docking station. The image processing device may be connected to a standard serial interface link, bus or network including and not limiting to USB, UART, SPI, IEEE 1394, Ethernet, etc to upload the images to the dental database.

BRIEF DESCRIPTION OF THE DRAWINGS

FIG. 3 is a view of the minimum embodiment of the digital dental intraoral system comprising an intraoral x-ray sensor (1), signal processing unit (2) powered from serial interface cable (6).

Figure 4:
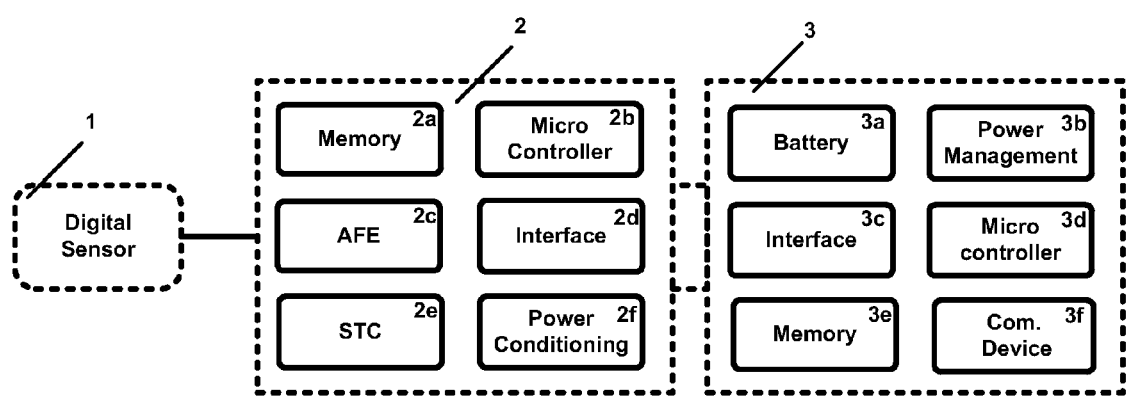
FIG. 4 shows the main functional blocks of the sensor system including the digital x-ray sensor (1), signal processing unit (2), power source unit (3).

The processing unit 2 at FIG. 4 incorporates analog front end (2c), sensor timing circuit (STC) (2e), controller (2b), memory (2a) interface circuit (2d) and power management (2f). The power source unit may consist of energy source (battery) (3a), power management (3b), interface circuit (3c), memory (3e), communication device (3f) and micro-controller (3d).

DETAILED DESCRIPTION OF THE INVENTION

FIG. 4 illustrates all components involved in operation of the dental imaging apparatus. The microcontroller (2b) at FIG. 4 manages the image acquisition process. The image is acquired when appropriate timing controls (2e) (clocks) are applied to the sensor and the analog frontend (2c) converts the analog sensor output to digital pixel values then those values are properly recorded in the memory (2a).

Some components from the signal processing unit (2) shown at FIG. 4 are duplicated into the battery unit (3) in order to support the image interface between the signal processing unit and the storage database (8). The controller (2b, 3d) is a device that manages the acquired data and synchronizes the readout process. The memory (2a, 3e) is present to store or help transfer the images from the sensor to the storage device. The interface circuit (2d, 3c) implements the actual interface of transferring the image to the file storage device. The power management (2f, 3b) delivers the power necessary for the operation of the system.

The energy source (3a) provides the electrical power necessary for the image acquisition process. The communication device (3f) allows wireless interface connection when the unit is operating. The microcontroller (2b, 3d) can provide indication as example a display for the image after the acquisition. The display can be displaying number of characters, illuminated light, like example light indication from light emitting diode (LED), with certain color or pattern or any similar visual or sound related feedback.

Figure 3:
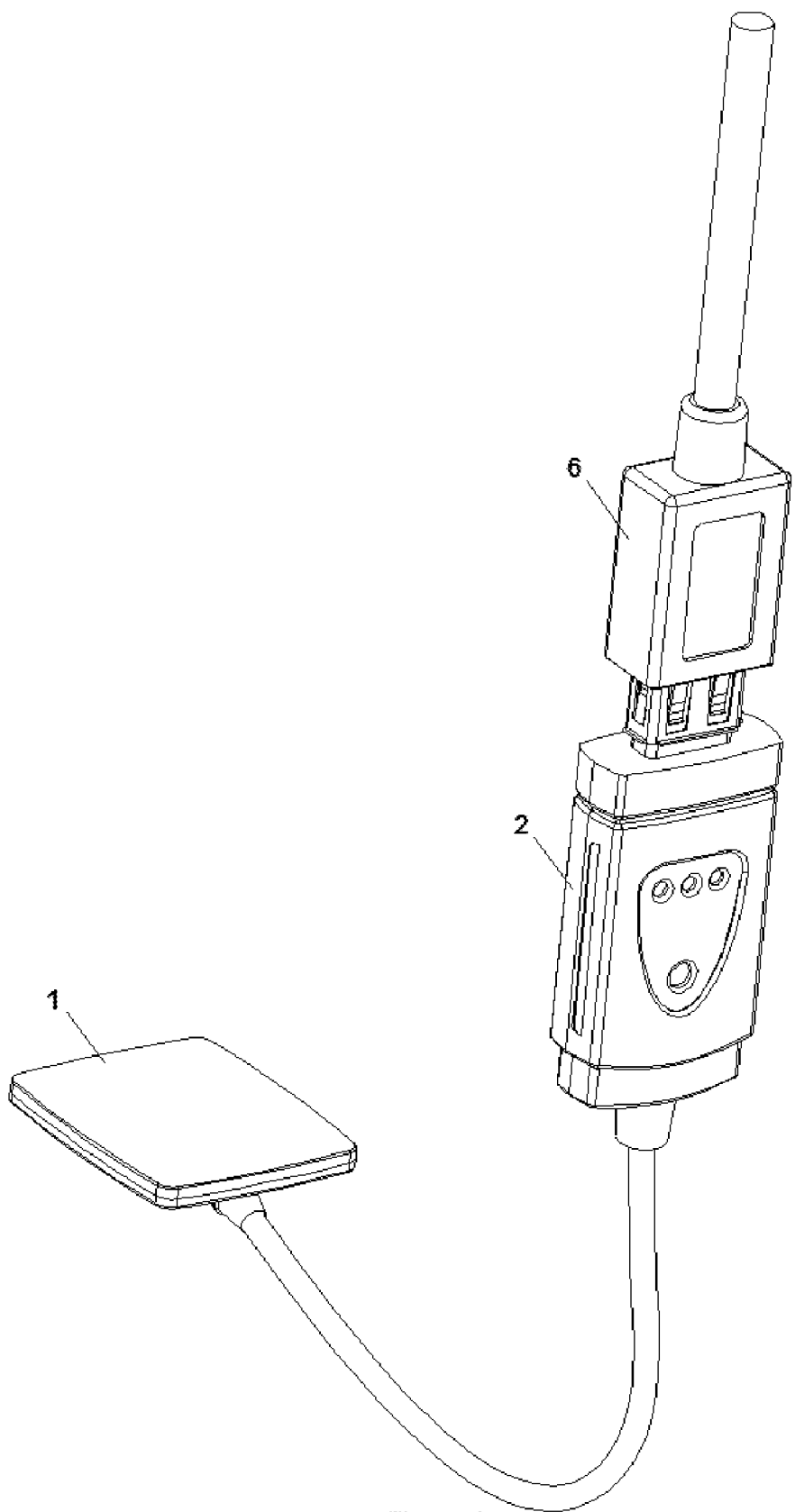
FIG. 3. The corresponding blocks are the same as in the previous paragraph.

Not all blocks at FIG. 4 are required. Minimum required blocks for the functionality of the device are 2a to 2f. In its minimum configuration the imaging apparatus will function according the embodiment shown at FIG. 3 where the sensor (1), image processor (2) will be attached to the positioning apparatus (sensor holder) (5) via the unit holder (clip) (4) and connected to the storage database (8) via the interface cable (6).

Figure 1:
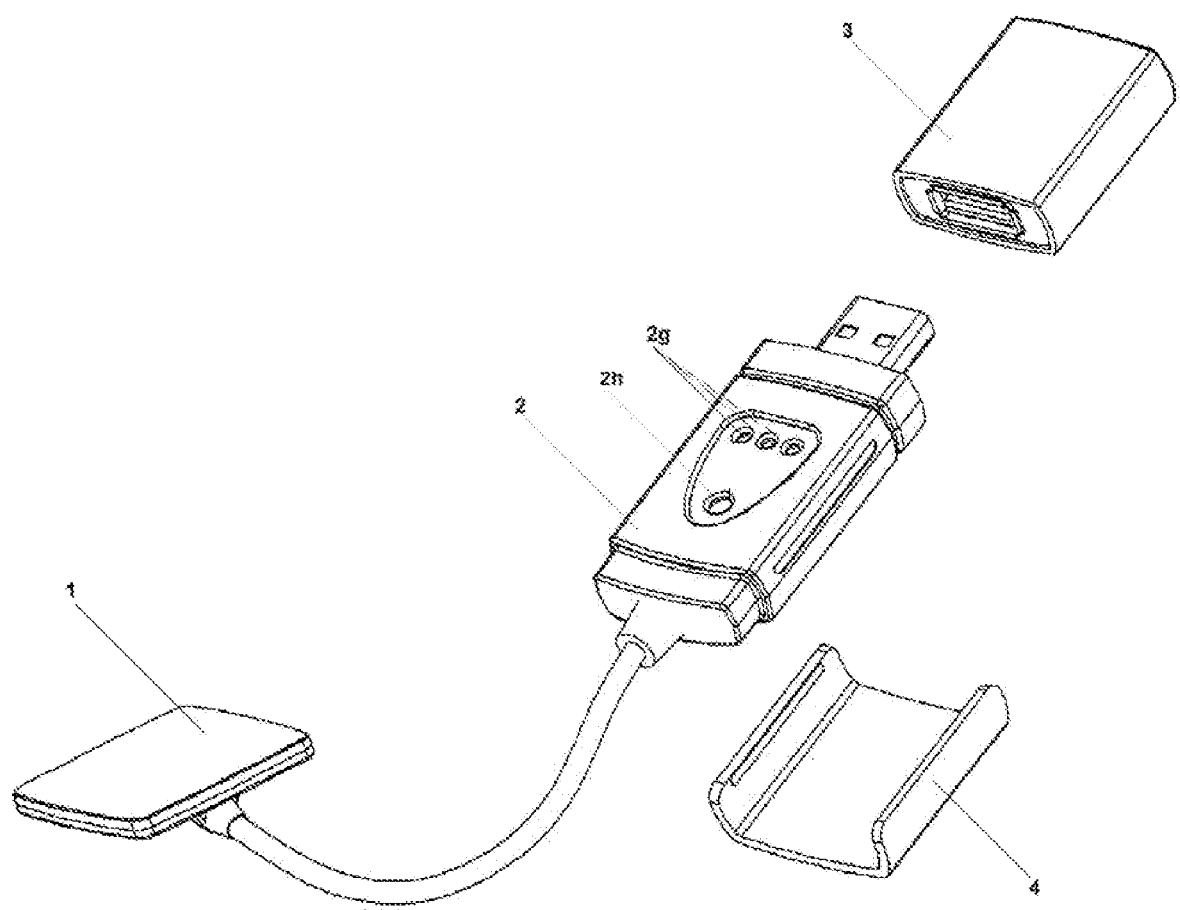
FIG. 1 is a view of a typical configuration of the digital dental intraoral system comprising an intraoral x-ray sensor (1), a signal processing unit (2), a power source (3) and a unit holder (4). The processing unit (2) shows multiple openings for light emitting diodes (LED) (2g) and a button (2f).
Figure 2:
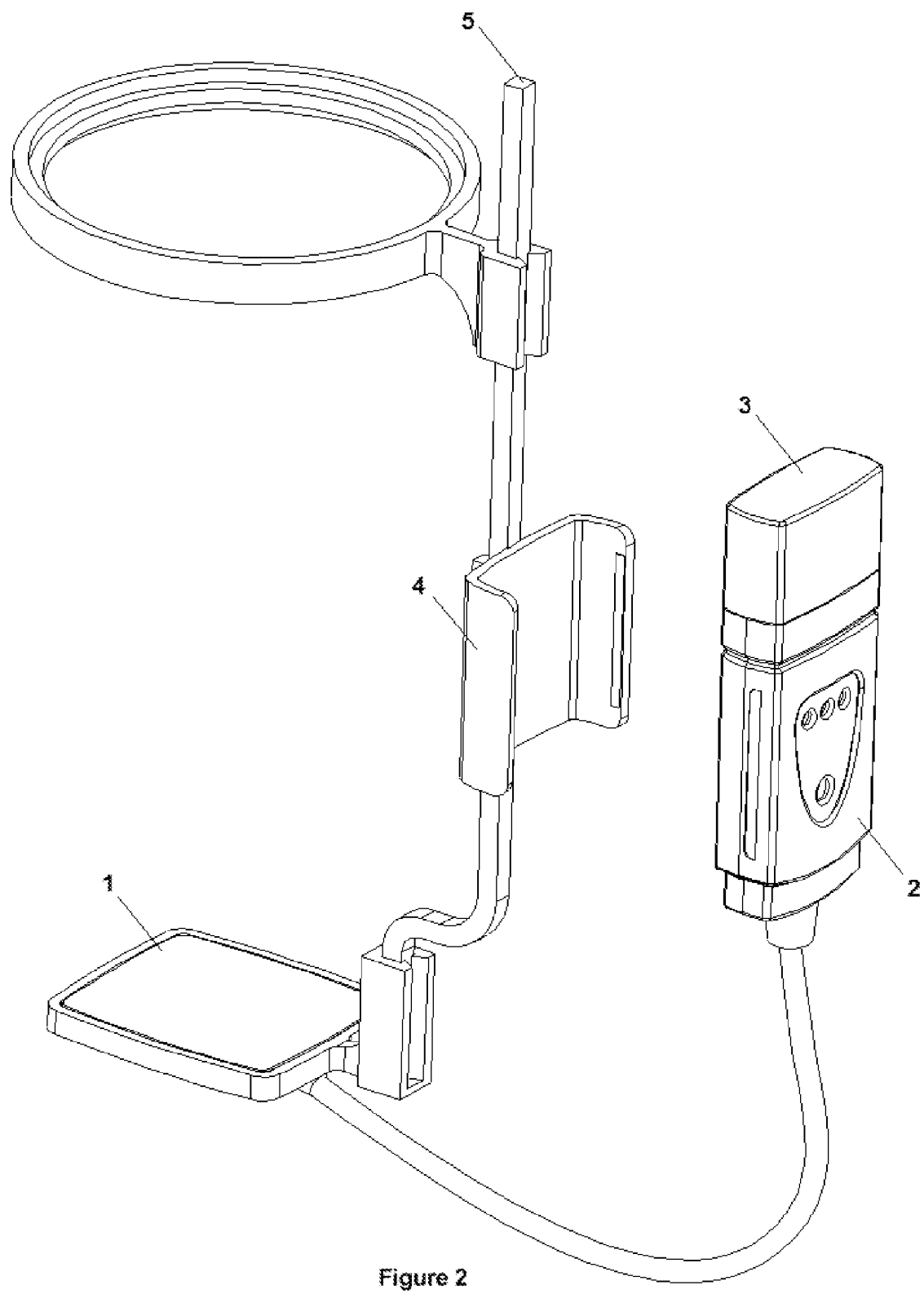
FIG. 2 is a view of the preferred embodiment of digital dental intraoral system comprising an intraoral x-ray sensor (1), signal processing unit (2) connected to a power source (3), sensor holder also called positioning apparatus (5) and unit holder (4) (clip) designed to attach to different positioning arm profiles.

The preferred embodiment of the system is shown at FIG. 2 where the image sensor (1) is placed at the sensor holder part of the positioning apparatus (5) and the unit holder (4) is installed on the sensor positioning apparatus (5). Both sensor (1) and the signal processing unit (2) with the unit holder (4) can be removed from the positioning arm (5). The light emitting diodes (2g) shown at FIG. 1 indicates the state in which the unit is operating. Button (2h) is shown at the signal processing unit enclosure.

The present invention has been particularly shown and described with reference to the minimum and preferred embodiments thereof, it will be understood by those of ordinary skill in the art that various changes in form and details may be made. The scope of the present invention is intended to be construed in connection with the attached claims and equivalents thereto.

What is claimed is:

1. A dental intraoral x-ray sensor system comprising:
   a sensor holder;
   a unit holder;
   a signal processing unit;
   a digital dental intraoral x-ray sensor; and
   a power source, wherein:
   said sensor holder is a positioning device comprising a rod and ring guide, said rod is designed to accommodate a variety of intraoral x-ray sensors and said rod allows said sensor to be adjusted to a variety of operative positions;
   said unit holder is designed to attach to said rod and accommodate said signal processing unit that is detachable from said unit holder;
   said signal processing unit comprising electronic components and said signal processing unit is coupled to said intraoral x-ray sensor via a sensor cable and to said power source via an electrical connector;
   said power source comprising a battery and controller circuitry encapsulated together in a cap detachably attached to a connector side of said signal processing unit; and
   said digital dental intraoral x-ray sensor comprising an encapsulated imaging pixel array attached to a distal end of said sensor cable.

2. The dental intraoral x-ray sensor system of claim 1, wherein said power source is detached from said signal processing unit and said signal processing unit is powered from a serial interface connector during an image acquisition using a serial interface cable.

3. The dental intraoral x-ray sensor system of claim 1, wherein said signal processing unit is powered from said power source during an image acquisition where said power source comprises a battery interconnect circuit located in a separate embodiment designed to accommodate a battery, a interface circuit, a micro controller, and a power management device that externally couples to said signal processing unit via said electrical connector.

4. The dental intraoral x-ray sensor system of claim 1, wherein said electrical connector comprises a standard USB type serial interface connector and said signal processing unit is powered during an image acquisition.

5. The dental intraoral x-ray sensor system of claim 1, wherein said signal processing unit is incorporating LED indication in a form of emitted light for an image quality.

6. The dental intraoral x-ray sensor system of claim 1, wherein said signal processing unit stores at least one full mouth image series in a local memory.

7. The dental intraoral x-ray sensor system of claim 1, wherein said power source is rechargeable via a serial interface connector, wherein said power source allows image data to be downloaded to storage database from an internal memory.

8. The dental intraoral x-ray sensor system of claim 1, wherein said signal processing unit has internal memory designed to store at least one full mouth image series and later transmit said full mount image series over a serial interface cable.

9. The dental intraoral x-ray sensor system of claim 1, wherein said power source has an internal memory, wherein said internal memory is designed to store at least one full mouth image series.

10. The dental intraoral x-ray sensor system of claim 1, wherein said signal processing unit has a wireless interface, wherein said wireless interface is built within with said signal processing unit and is designed to transfer full mouth image series to a storage database.

11. The dental intraoral x-ray sensor system of claim 1, wherein said power source has a wireless interface, wherein said wireless interface is built within.

12. A dental x-ray system for image acquisition comprising:
   a sensor holder;
   a unit holder;
   a signal processing unit;
   a digital dental intraoral x-ray sensor;
   a power source; and
   an internal memory; wherein:
   said sensor holder is a positioning device comprising a rod and a ring guide, said rod is designed to accommodate a variety of intraoral x-ray sensors and said rod allows said sensor to be adjusted to a variety of operative positions;
   said unit holder is designed to attach to said rod and accommodate said signal processing unit that is detachable from said unit holder;
   said signal processing unit comprising electronic components and said signal processing unit is coupled to said intraoral x-ray sensor via a sensor cable and to said power source via an electrical connector;

said power source comprising a battery and controller circuitry encapsulated together in a cap detachably attached to a connector side of said signal processing unit;

said digital dental intraoral x-ray sensor comprising an encapsulated imaging pixel array attached to a distal end of said sensor cable; and wherein said signal processing unit includes said internal memory, wherein multiple images are stored on said internal memory.

13. The dental x-ray system of claim 12, wherein said images are digitally formatted and saved into said internal memory as conventional image files during a process of taking dental image series.

14. The dental x-ray system of claim 12, wherein said images are saved in said internal memory after being digitally formatted and processed from said signal processing unit in order to be retrieved from said memory without need of proprietary interface.

15. The dental x-ray system of claim 12, wherein said internal memory is designed to store images for at least one full mouth image series during a process of taking a dental image series.

16. The dental x-ray system of claim 12, wherein said processing unit has LED feedback in a form of emitted light as an indication for an image quality.

17. The dental x-ray system of claim 12, wherein said processing unit allows images to be cancelled during a process of taking dental image series based on LED feedback in a form of emitted light for an image quality.

18. The dental x-ray system of claim 12, wherein said processing unit allows images to be repeated during a process of taking dental image series based on LED feedback in a form of emitted light.

19. The dental x-ray system of claim 12, wherein said processing unit allows images to be deleted during a process of taking dental image series based on LED feedback in a form of emitted light.

\* \* \* \* \*